US006436406B1

(12) United States Patent
Yegorova

(10) Patent No.: US 6,436,406 B1
(45) Date of Patent: Aug. 20, 2002

(54) COMPOSITIONS AND METHODS FOR REDUCING OR CONTROLLING BLOOD CHOLESTEROL, LIPOPROTEINS, TRIGLYCERIDES AND ATHEROSCLEROSIS

(75) Inventor: Inna Yegorova, Northridge, CA (US)

(73) Assignee: A. Glenn Braswell, Miami, FL (US)

( * ) Notice: Subject to any disclaimer, the term of this patent is extended or adjusted under 35 U.S.C. 154(b) by 0 days.

(21) Appl. No.: 09/594,585

(22) Filed: Jun. 15, 2000

(51) Int. Cl.$^7$ ............................................... A01N 65/00
(52) U.S. Cl. .................... 424/195.1; 424/646; 514/690; 514/456; 514/168
(58) Field of Search ............................. 424/195.1, 646; 514/690, 456, 168

(56) References Cited

U.S. PATENT DOCUMENTS

| | | | |
|---|---|---|---|
| 4,235,871 A | | 11/1980 | Papahadjopoulos et al. |
| 4,708,861 A | | 11/1987 | Popescu et al. |
| 4,997,655 A | | 3/1991 | Nagy et al. |
| 5,135,945 A | * | 8/1992 | Robinson et al. ........... 514/456 |
| 5,248,688 A | | 9/1993 | Dudrick |
| 5,853,755 A | | 12/1998 | Foldvari |
| 5,922,342 A | | 7/1999 | Shah et al. |
| 6,020,324 A | | 2/2000 | Jamas et al. |
| 6,020,383 A | | 2/2000 | Stone et al. |
| 6,046,022 A | * | 4/2000 | Zhang et al. .................. 435/41 |
| 6,048,846 A | * | 4/2000 | Cochran ....................... 514/168 |
| 6,143,301 A | * | 11/2000 | De La Harpe et al. .. 424/195.1 |
| 6,156,802 A | * | 12/2000 | Mae et al. ................... 514/690 |
| 6,197,309 B1 | * | 3/2001 | Wheeler ................... 424/195.1 |
| 6,203,819 B1 | * | 3/2001 | Fine ........................... 424/646 |

FOREIGN PATENT DOCUMENTS

| | | |
|---|---|---|
| WO | WO 98/14177 | 4/1998 |

OTHER PUBLICATIONS

American Heart Assoc., 2000, http://www.american-heart.org/Heart_and_stroke_A_Z_Guide/vvds.html.
Gonzalez & Kannewurf, 55(Suppl. 1) Am. J. Health–Sys. Pharm. S4–S7 (1991).
Caracciolo et al., 91(9) Circulation 2335–44 (1995).
Marcovina & Morrisett, 6 Curr. Opin. Lipidol. 136–45 (1995).
Goodman & Gilman's The Pharmacological Basis of Therapeutics (J. Hardman & L. Lipman, 9$^{th}$ ed. 1996).
Austin, 83(9B) Amer. J. Cardiol. 13F–16F (1999).
Illingworth, 41(2) Drugs 151–60 (1991).
Expert Panel on Detection, Evaluation, and Treatment of High Blood Cholesterol in Adults, 269(23) J. Amer. Med. Assoc. 3015–23 (1993).
Frohlich & Pritchard, 22 Clin. Biochem. 417–23 (1989).
Dietschy, 65 Amer. J. Clin. Nutr. 1581S–9S (1997).
Steinberg et al., 320(14) New Eng. J. Med. 915–24 (1989).
Mortensen et al., 18 Mol. Aspects Med. s137–s144 (1997).
Steinberg et al., 321(17) New Eng. J. Med. 1196–97 (1989).
Salonen et al., 339(8798) Lancet 883–87 (1992).
Parthasarathy et al., 6(5) Arteriosclerosis 505–10 (1986).
Carew et al., 84 Proc. Nat'l Acad. Sci. USA 7725–29 (1987).
Steinbrecher et al., 81 Proc. Nat'l Acad. Sci. 3883–87 (1984).
Cathcart et al., 38 J. Leukocyte Biol. 341–50 (1985).
Pryor, 28(1) Free Radical Biol. & Med. 141–64 (2000).
Witztum & Steinberg, 88(6) J. Clin. Invest. 1785–92 (1991).
Bruce et al., 19(1) J. Amer. Coll. Nutr. 18–23 (1999).
Knopp et al., 17(1) Amer. J. Prev. Med. 18–23 (1999).
Burton & Mannien, 668(Suppl.) Acta Medica Scandinavica 91–94 (1982).
MRC/BHF Heart Protection Study Collaborative Group, 20(10) Eur. Heart J. 725–41 (1999).
Azen et al., 94(10) Circulation 2369–72 (1996).
Hodis et al., 273(23) J. Amer. Med. Assoc. 1849–54 (1995).
Kothari & Jain,28(1) Acta Biol. Acad. Sci. Hung. 111–14 (1977).
Stefanutti et al., 149(2) Clin. Ter. 115–19 (1998).
Elisaf et al., 18(5) Amer. J. Nephrol. 416–21 (1998).
Leng et al., 4(4) Vas. Med. 219–26 (1999).
Morcos, 89(10) J. Nat. Med. Assoc. 673–78 (1997).
Endo, 32(8) J. Antibiotics 852–54 (1979).
Endo et al., 39(12) J. Antibiotics 1670–73 (1986).
Davignon et al., 73 Prev. Cardiol. 339–45 (1994).
Dujovne et al., 91(Supp. 1B) Amer. J. Med. 25S–30S (1991).
http://star.scl.kyoto–u.ac.jp (2000).
Herber et al., 69 Amer. J. Clin. Nutr. 231–36 (1999).
Li et al., 18(1) Nutr. Res. 71–81 (1998).
Wang et al., 58(12) Curr. Ther. Res. 964–78 (1997).
Greenberg & Frishman, 30 J. Clin. Pharmacol. 596–08 (1990).
Folkers et al., 2 J. Mol. Med. 431–60 (1977).
Palomäki et al., 39 J. Lipid Res. 1430–37 (1998).
de Rijke et al., 17(1) Arteriosclerosis, Thrombosis, and Vascular Biology 127–33 (1997).
Bargossi et al., 15(Suppl.) Mol. Aspects Med. s187–s193 (1994).
Alleva et al., 92 Proc. Nat'l Acad. Sci. USA 9388–91 (1995).
Langsjoen et al., 15(Supp.) Mol. Aspects Med. s165–s175 (1994).
Meydani, 345(8943) Lancet 170–75 (1995).
Jha et al., 123(11) Ann. Int. Med. 860–72 (1995).
Salonen et al., 91(3) Circulation 645–55 (1995).

(List continued on next page.)

*Primary Examiner*—Christopher R. Tate
*Assistant Examiner*—Randall Winston
(74) *Attorney, Agent, or Firm*—Sierra Patent Group, Ltd.

(57) ABSTRACT

This invention provides compositions and methods related to the administration of red yeast rice, coenzyme $Q_{10}$, and chromium, with or without inositol hexanicotinate, selenium, and mixed tocopherols to reduce or control blood cholesterol, triglycerides, low density lipoproteins, or increasing or controlling high density lipoproteins in a manunal, to reduce arterial plaque build-up, atherosclerosis, in a mammal which may be associated with cardiovascular, cerebrovascular, peripheral vascular, or intestinal vascular disorders.

13 Claims, No Drawings

OTHER PUBLICATIONS

Salvini et al., 76(17) Amer. J. Cardiol. 1218–21 (1995).
Newman et al., 24(4) Clin. Chem. 541–44 (1978).
Press et al., 152(1) West. J. Med. 41–45 (1990).
Lee & Reasner, 17(12) Diabetes Care 1449–52 (1994).
Anderson et al., 46(11) Diabetes 1786–91 (1997).
Gotto Jr., 82(9A) Am. J. Cardiol. 22Q–25Q (1998).
Zema, 35(3) J. Amer. Coll. Cardiol. 640–46 (2000).
Alleva et al., 92 Proc. Natl. Acad. Sci., USA 9388–9391 (1995).
de Grey, 1(1) J. Anti–Aging Med. 53–66 (1998).
Endo et al., 38(3) J. Antibiotics 444–448 (1985).
Gardner et al., 31 Ann. Pharmacother. 677–682 (1997).
Goodman & Gilman's The Pharmacological Basis Of Therapeutics (J. Hardman & L. Lipman, 9$^{th}$ ed. 1996)., Tables 6–1, 6–4.
Hiramatsu et al., 7(1) Arteriosclerosis 55–60 (1987).
Ilarionov et al., 28(2) Eksperim. Med. Imorf. 52–56 (1989) (translation).
Morehouse et al., 40 J. Lipid Res. 464–474 (1999).
Palinski et al., 86 Proc. Natl. Acad. Sci. USA 1372–1376(1989).
Parthasarathy et al., 82 Proc. Natl. Acad. Sci. USA 3000–3004 (1985).
Porta et al., Lipofuscin And Ceroid Pigments (E. Porta, Ed. 1990)., pp. 169–190.
Qureshi et al., 53 Am. J. Clin. Nutr. 1042S–1046S (1991).
Steinbrecher et al., 81 Proc. Natl. Acad. Sci. USA 3883–3887 (1984).
Steinbrecher et al., 25 J. Lipid Res. 1109–1116 (1984).
Wang et al., 1(1) Chin. J. Exp. Ther. Prep. Chin. Med. 1–5 (1995) (translation).
Endo et al., 38(3) J. Antibiotics 420–422 (1985).

\* cited by examiner

COMPOSITIONS AND METHODS FOR REDUCING OR CONTROLLING BLOOD CHOLESTEROL, LIPOPROTEINS, TRIGLYCERIDES AND ATHEROSCLEROSIS

FIELD OF INVENTION

This invention relates to compounds and methods that reduce or control levels of cholesterol and triglycerides and their oxidation to lipid peroxidases, thus preferably inhibiting or arresting the development of atherosclerosis and restenosis when administered to mammals, including humans.

BACKGROUND OF THE INVENTION

The present invention relates generally to compositions and methods for treating atherosclerosis; more particularly, it relates to methods and compositions for treating or preventing atherosclerosis whereby the many and varied problems associated with the disease can be prevented, arrested, substantially alleviated or cured.

In the United States and Western Europe, cardiovascular disease and its associated maladies, dysfunctions and complications are a principal cause of disability and the chief cause of death. One specific entity significantly contributing to this pathophysiologic process is atherosclerosis, which has been generally recognized as the leading health care problem both with respect to mortality and health care costs. The American Heart Association estimates that 953,110 persons died of cardiovascular diseases in 1997 (41.2 percent of all deaths), more than the number of mortality for cancer (539,377), accidents (95,644) and HIV (16,516) combined. Furthermore, by association calculations, close to a quarter of the US population suffers from one or more forms of cardiovascular disease. AMERICAN HEART Assoc., 2000, http://www.americanheart.org/Heart_and_Stroke_A_Z_Guide/cvds.html. The medical costs associated with coronary heart disease are estimated at $95 billion dollars a year. Gonzalez & Kannewurf, 55 (19) AMERICAN JOURNAL OF HEALTH-SYSTEM PHARMACY S4-7 (Supp. 1, 1998).

Atherosclerosis is a disease characterized by the deposition of fatty substances, primarily cholesterol, and subsequent fibrosis in the inner layer (intima) of an artery, resulting in plaque deposition on the inner surface of the arterial wall and degenerative changes within it. The ubiquitous arterial fatty plaque is the earliest lesion of atherosclerosis and is a grossly flat, lipid-rich atheroma consisting of macrophages (white blood cells) and smooth muscle fibers. The fibrous plaque of the various forms of advanced atherosclerosis has increased intimal smooth muscle cells surrounded by a connective tissue matrix and variable amounts of intracellular and extracellular lipid. At the luminal surface of the artery, a dense fibrous cap of smooth muscle or connective tissue usually covers this plaque or lesion. Beneath the fibrous cap, the lesions are highly cellular consisting of macrophages, other leukocytes and smooth muscle cells. Deep in this cell-rich region may be areas of cholesterol crystals, necrotic debris and calcification.

If allowed to progress, the disease can cause narrowing and obstruction of the lumen of the artery, diminished or occluded blood flow and, consequently, ischemia or infarction of the predominantly affected organ or anatomical part such as the brain, heart, intestine or extremities. The result can be significant loss of function, loss of cellular substance, emergency medical and/or surgical procedures, and significant disability or death. Alternatively, the arterial wall can be severely weakened by the infiltration of the muscular layer with the lipid (cholesterol), inflammatory white blood cells, connective tissue and calcium, resulting in soft and/or brittle areas which can become segmentally dilated (aneurysmal) and rupture or crack leading to organ, limb or even life-threatening hemorrhage.

Once the disease has progressed to the stage of significant persistent symptoms and compromised function, the next treatment step has conventionally been artery bypass grafting to repair and/or replace the damaged artery. While coronary artery bypass has become one of the more common major cardiovascular surgical procedures in the United States, surgery clearly is not the solution to the pathologic process. Moreover, there is a significant risk of morbidity and mortality associated with surgery that many patients are reluctant to accept. Indeed, the autogenous veins or arteries used to bypass the disease-impaired arteries undergo atherosclerosis changes postoperatively generally at a faster rate than the original, affected arteries. The Coronary-Artery Surgery Study (CASS) sponsored by the National Heart, Lung and Blood Institute (NHLBI) concluded that certain subsets of patients do not gain any overall statistical benefit from bypass surgery in comparison to other medical treatments. Carraciolo, 91(9) CIRCULATION 2335–44 (1995).

As an alternative to coronary bypass surgery, certain medications and procedures are used to treat the results of atherosclerosis. These treatments include chelation with ethylene diamine tetra-acetic acid (EDTA) and percutaneous transluminal coronary angioplasty (PTCA). EDTA treatments, however, are still experimental, unproved and potentially as harmful as they are beneficial. PTCA treatments are invasive, of limited application and success and occasionally manifest lethal complications. Highly experimental intra-arterial laser beam plaque vaporization has limited application and requires an open operative approach to affected vessels.

It is now well established that vascular blockage and cardiovascular disorders including myocardial infarction, coronary heart disease, hypertension and hypotension, cerebrovascular disorders including stroke, cerebral thrombosis and memory loss due to stroke; peripheral vascular disease and intestinal infarction are caused by blockage of arteries and arterioles by atherosclerotic plaque. The production of atherosclerotic plaque formation is multi-factorial in its production. Hypercholesterolemia, especially elevated levels of low-density lipoprotein cholesterol (LDL) is an important risk factor for atherosclerosis and arteriosclerosis and associated diseases.

Lipoproteins are spherical particles with the non-polar triglycerides and cholesteryl esters in the hydrophobic core, the polar lipids, phospholipids and free cholesterol on the surface with apolipoproteins. When the amount of cholesterol entering the body increases, the pools of sterol within liver cells expands and the receptors that clear LDL from the blood down-regulate, thus increasing LDL levels in the blood. When cholesterol intake is constant, some long-chain saturated fatty acids further suppress the hepatic LDL receptor whereas several unsaturated fatty acids have the opposite effect. Lipoprotein (a) [Lp (a)] has emerged as a plasma lipoprotein linked to both diseases of the coronary arteries, the carotid and the cerebral arteries. It is structurally related to LDL and possesses one molecule of apolipoprotein $B_{100}$ per particle. Macrophages express the scavenger receptor that readily recognizes oxidatively modified Lp (a). Marcovina & Morrisett, 6 CURRENT OPINION IN LIPIDOLOGY 136–145 (1995).

Cholesterol levels below 200 mg/dl are considered "desirable." A Scandinavian study showed that reduction of cholesterol reduced mortality associated with coronary artery disease (CAD) by 42% over six year period and reduced overall mortality by 30%. GOODMAN & GILMAN'S THE PHARMACOLOGICAL BASIS OF THERAPEUTICS (J. Hardman & L. Lipman, 9$^{th}$ ed. 1996) [Hereinafter "J. Hardman"]. Researchers have shown that a 1-mMol/L increase in triglyceride levels produces a 76% increase in cardiovascular disease risk in women and a 31% increase in men. Austin, 83 (9B) AMERICAN JOURNAL OF CARDIOLOGY 13F–16F (1999). Even in patients with established disease, lowering of LDL cholesterol to between 2 and 2.5 mmol/L retards its progression and may even lead to regression. Illingsworth, 41(20) DRUGS 151–160 (1991).

It is recommended that persons with elevated cholesterol concentrations above 240 mg/dL (6.2 mM/L) receive treatment and that those with borderline values between 200–239 mg/dL (5.2 to 6.2 mM/L) be further evaluated according to the presence of risk factors for coronary artery disease including the sex of the patient, post-menopausal status, a low plasma concentration of HDL cholesterol (below 35 mg/dL [0.9 mM/L]), positive family history, smoking, hypertension and diabetes mellitus. Expert Panel on Detection, Evaluation, and Treatment of High Blood Cholesterol in Adults, 269(23) J. AM. MEDICAL A. 3015–3023 (1993). Other factors include obesity, hypertriglyceridemia, sedentary lifestyle, steroid use, β-adrenergic blocking agents, some diuretics and genetic factors. Frohlich & Pritchard, 22 CLINICAL BIOCHEMISTRY 417–433 (1989).

By the 1980's, it was recognized that HDL levels could be more important in predicting atherosclerotic disease than LDL and that HDL may prevent the development of CAD. Id. Factors such as smoking, obesity, hypertriglyceridemia, genetic factors and lack of exercise are major causes of reduced serum HDL. HDL cholesterol lipoproteins move excess cholesterol from the extrahepatic organs to the liver for excretion. Dietschy, 65 AM. J. CLINICAL NUTRITION 1581S-9S (1997). There is evidence that virtually every body tissue is capable of at least some cholesterol synthesis from the precursor acetyl-coenzyme A (CoA). Every day, HDL carries back to the liver an amount of cholesterol equal to the amount synthesized and taken up as LDL by all extrahepatic organs except endocrine glands. There is a second LDL transport process that is receptor independent. Id. Removal of free cholesterol from arterial wall cells may be an important mechanism by which HDL plays an anti-atherogenic role. J. Hardman, supra, at 878.

The earliest recognized gross lesion in atherogenesis is the fatty streak, characterized by an accumulation of cells loaded with cholesteryl esters ("foam cells") just beneath the vascular endothelium. The LDL receptor in the arteries gives rise to foam cells and fatty streaks, the earliest lesion in atherosclerosis, but there is also a receptor-independent mechanism for their formation. This has been demonstrated by the development of lesions rich in macrophage-derived foam cells, even in patients and animals deficient in LDL receptors, and the failure to produce foam cells from normal monocytes and monocyte derived macrophages incubated with LDL. This led researchers to explore the possibility of a post-secretory modification of LDL before it is taken up into foam cells by a new, specific receptor: the "scavenger receptor." Steinberg, 320(14) NEW ENG. J. MEDICINE 915–924 (1989).

Researchers have shown that when LDL was incubated with cultured endothelial cells it underwent a striking series of physical and chemical changes and was taken up by cultured macrophages 10 times more rapidly than native LDL. Id., at 916. At any given level of hypercholesterolemia there is considerable variation in clinical disease. Postsecretory modifications in the structure of lipoproteins appear to effect their atherogenic potential. Steinberg, supra, at 915. It is not only the elevated levels of LDL cholesterol that are important, but also its oxidation that leads to atherosclerosis. For this reason antioxidants are believed to reduce the risk of atherosclerotic disease. Mortensen, 18 MOLECULAR ASPECTS OF MEDICINE s137–s144, (Supp.1997). Peroxidation of polyunsaturated fatty acids in the LDL lipids is the common initiating factor of the changes and the cytotoxicity of oxidized LDL has been proven by several research groups and may lead to the denudation of the benign fatty-streak lesion into the atheromatous plaque. Steinberg, supra, at 918.

Researchers believe that the oxidation of LDL within the arterial wall itself is most important. Ocana, 321(17) NEW ENG. J. MEDICINE 1196–1197 (1989). Auto-antibodies to MDL-LDL were seen at significantly higher titers in men with atherosclerosis than in normal controls, and in a greater proportion of smokers, those with higher LDL cholesterol, and those with higher serum levels of copper in the case group. Salonen, 339 LANCET 883–887 (1992).

Researchers also have studied the effects of incubation of LDL with macrophages and found that in that environment LDL is oxidized and recognized and taken up by the acetyl LDL or scavenger receptor in the same cell. Alpha-tocopherol, butylated hydroxytoluene (BHT) and Probucol block this process. Parthasarathy, 6(5) ARTERIOSCLEROSIS 505–10 (1986). Treatment with Probucol, a potent antioxidant, significantly lowered the rate of development of fatty streak lesions in hyperlipidemic rabbits, although the plasma cholesterol level was not lower than in lovastatin-treated animals. Carew, Schwenke & Steinberg, 84 PROC. NAT'L ACAD. SCI. USA 7725–7729 (1987). Similar results have been demonstrated in cultures of LDL with endothelial cells. Steinbrecher, 81 PROC. NAT'L ACAD. SCI. 3883–3887 (1984). Monocytes and neutrophils, when incubated with LDL, oxidize LDL and render it toxic. Cathcart, Morel & Chisolm, 38 J. LEUKOCYTE BIOLOGY 341–350 (1985).

Vitamin E, a potent antioxidant, has been shown to reduce the extent of atherosclerosis in several animal models and studies have shown that Vitamin E can be protective against the disease. Pryor 28(1) FREE RADICAL BIOLOGY & MEDICINE 141–64 (2000). The development of the fatty streak lesion may be based upon two factors: the presence of elevated plasma LDL and its oxidative modification within the artery wall. Steinberg, supra, at 919. LDL particles in whole plasma contain the antioxidant compounds vitamin E and β-carotenes and the plasma itself contains antioxidants that protect the LDL for a relatively short time. Under pro-oxidant conditions, the vitamin E and β-carotene are destroyed before the fatty acids undergo peroxidation. Id., at 921. It is likely that decreases in vitamin E and beta-carotene are early events reflecting the initial stages of lipid peroxidation. Witztum & Steinberg, 88(6) J. CLINCAL INVESTIGATION 1785–1792 (1991).

Common medications used to lower plasma cholesterol levels include Atromid-S® (clofibrate), Choloxin® (dextrothyroxine sodium), Colestid®, (colestipol hydrochloride), Lopid®(gemfibrozil), Lorelco®, (probucol), Nicolar® (Niacin/nicotinic acid) and Questran® (Cholestyramine resin). These drugs and their associated treatments, however, generally are directed only at the cause, and not the result, of atherosclerosis and have not been shown to be effective in reversing the plaque deposition and degenerative changes in the arterial walls. These pharmacological agents also have many other shortcomings such as, for example, adverse side effects (hypertension, cardiac arrhythmias, gastrointestinal disturbances, headache, hypersensitivity, etc. . . ), contraindications (heart, liver or kidney disease, pregnancy, etc. . . ), requirement for lifelong conscientious administration, difficulty in maintaining consistent patient compliance, variable reliability and high cost.

Other therapies have been used to lower cholesterol levels. These include: dietary changes, Bruce, 19(1) JOURNAL OF THE AMERICAN COLLEGE OF NUTRITION 61–7 (2000); fiber and psyllium, Knopp, 17(1) AMERICAN JOURNAL OF PREVENTIVE MEDICINE 18–23 (1999), Burton & Mannien, 668 MEDICA SCANDINAVICA 9104 (Supp. 1982); Vitamins C, E, and carotenoids, Anonymous 20(1) European Heart Journal 725–41 (1999), Azen, 94(10) CIRCULATION 2369–72 (1996), Hodis, 273(23) J. AM. MEDICAL A 1849–54 (1995), Kothari 28(1) ACTA BIOLOGICA ACADEMIAE SCIENTIARUM HUNGARICAE 111–4 (1977); L-carnitine, Stefanutti, 149(2) CLINICA TERAPEUTICA 115–9 (1998), Elisaf, 18(5) AM. J. NEPHROLOGY 416–21 (1998); fatty acids, Leng, 4(4) VASCULAR MEDICINE 219–26 (1999); fatty acids eicosapentanoic acid (fish oil) and garlic, Morcos, 89(10) J. NAT. MEDICAL A. -673–8 (1997);.beta glucan, U.S. Pat. No. 6,020,324 to Jamas, et.al.; and, amino acids, U.S. Pat. No. 5,248,688 to Dudrick.

Bile acid-binding resins, such as cholestyramine, promote bile acid excretion and were shown to produce a 20% decrease in LDL. This treatment, however, lead to a compensatory increase in the number of hepatic LDL receptors and induction of HMG-CoA Reductase activity, which may bind other negatively charged anions and hence decrease the absorption of therapeutic drugs. J. Hardman, supra, at 890–1.

U.S. Pat. No. 6,020,383, to Stone, states that a substance used as an antioxidant in food and in cosmetics and to inhibit polymerization of polyesters, tert-butylhydroquinone ("TBHQ"), was shown to unexpectedly reduce blood cholesterol and triglycerides in rats. The inventor further discusses the use of TBHQ in combination with other natural oxidants including vitamins C and E, tocopherols, and Coenzyme $Q_{10}$.

The HMG-CoA Reductase inhibitors have been used with some success in reducing blood levels of LDL cholesterol and raising HDL levels. Cholesterol is produced via the mevalonic acid pathway. Reducing the formation of mevalonic acid, a precursor to cholesterol, leads to a corresponding decrease in hepatic cholesterol biosynthesis with a reduction in the cellular pool of cholesterol. There is a compensatory increase in the number of high affinity LDL receptors expressed on the cell surface, stimulating an increase in catabolism of VLDL remnants and LDL, and possibly a reduced hepatic synthesis. Illingsworth, supra.

The first specific competitive inhibitors of HMG CoA Reductase that were tested in human subjects were mevastatin (isolated from cultures of *Penicillium citrinum*) and lovastatin (isolated from cultures of *Aspergillis terreus* and *Monascuspurpurea*). Endo, 32(8) J. ANTIBIOTICS 852–4 (1979). A related compound, Monacolin M, was isolated from culture of *Monascus* ruber in 1986. Endo, Komagata & Shimae, 39(12) J. ANTIBIOTICS 1670–3, (1986). Mevastatin, however, was withdrawn from clinical use in Japan because of rumored changes in intestinal morphology in dogs, although similar effects were not seen with lovastatin. Illingsworth, supra, at 152. The efficacy of the other HMG-Reductase inhibitors is documented. Lovastatin was shown to decrease levels of VLDL by 53% and LDL by 32.4%, and simvastatin was shown to decrease cholesterol by 34% and triglycerides by 39%, yet the concentration of Lp (a) rose in some patients. Id., at 155. Side effects include headaches, transient changes in bowel habits, nausea, insomnia, and less commonly muscle tenderness and increased plasma creatine kinase. Illingsworth, supra, at 157.

Pravastatin has also been combined with nicotinic acid (niacin) to increase reductions in serum cholesterol. Davignon, 73 PREVENTIVE CARDIOLOGY 339–345, (1994). Lovastatin was shown to be safe and effective in reducing total cholesterol and LDL while raising HDL, but side effects included increased liver transaminase levels (in 2%), myopathy with a creatine kinase greater than 10 times normal (in 0.5% of subjects) and required discontinuation in 9% of those treated. The authors confirmed the need to monitor liver function tests every 4–6 weeks in patients on lovastatin therapy. Dujovne, 91 AM. J. MEDICINE 25S–30S (Supp. 1B, 1991).

A serious shortcoming of the HMG CoA Reductase inhibitors, including the more natural *Monascus*, is the unavoidable depletion of Coenzyme $Q_{10}$. This is because Coenzyme $Q_{10}$ is synthesized from acetyl-CoA through mevalonate and isopentenylpyrophophate, as is cholesterol. By inhibiting the production of mevalonate to reduce cholesterol, it follows that there is less to form Coenzyme $Q_{10}$ as well. Mortensen, supra.

SUMMARY OF THE INVENTION

The inventor has now discovered that appreciating the multi-factorial genesis of cholesterol elevation and affecting several phases of cholesterol production simultaneously with a composition of natural substances is a way to effectively control cholesterol levels. A method of altering the concentration of the cholesterol constituents in the blood of a human to reduce the risk of atherosclerosis and vascular disease is provided. A composition comprising red yeast rice, Coenzyme $Q_{10}$, and mixed tocopherols, with or without one or more selected from the group consisting of selenium, inositol hexanicotinate or chromium, is administered to a human in an amount effective to reduce or control blood cholesterol, to increase the concentration of HDL-cholesterol and/or to decrease the concentration of LDL-cholesterol in the blood of the human.

In accordance with the present invention, methods and compositions are provided for use in treating atherosclerosis and its associated diseases including cardiovascular disorders, cerebrovascular disorders, peripheral vascular disorders, and intestinal vascular disorders. The methods and compositions of the present invention are particularly advantageous in that they may be used to both significantly lower plasma cholesterol levels and substantially arrest, reverse and/or cure the arterial plaque deposition and degenerative vascular wall changes associated with atherosclerosis.

The compositions of the present invention can be administered prophylactically, so as to inhibit atherogenesis or restenosis, or therapeutically after atherogenesis has been initiated. Thus, for example, a patient who is to undergo balloon angioplasty can have a regimen of the composition administered substantially prior to the balloon angioplasty, preferably at least about a week or substantially longer. Alternatively, in a patient where atherogenesis is suspected, the administration the composition can begin at any time. Administration may be accomplished in any manner known to those skilled in the art, including peroral, liposomal, inhalation, sublingual, rectal (e.g., suppositories), or through an oral spray or dermal patch.

Methods are provided for modulating the production of LDL-cholesterol through inhibition of HMG-Reductase, enhancing levels of HDL-cholesterol, replacing the resulting deficiency of Coenzyme $Q_{10}$, supplying anti-oxidants mixed tocopherols with or without selenium to reduce the oxidation of LDL into lipid peroxidases, and normalizing carbohydrate metabolism through the administration of chromium and/or inositol hexanicotinate. As a prophylactic or treatment for atherosclerotic susceptible hosts, the composition is chronically administered at an effective dosage. For restenosis, the agent may be administered for a limited period since this pathological process generally abates 3–6 months after the vascular injury (i.e., angioplasty or atherectomy).

In one embodiment of the invention, the composition is administered to a human in one or more tablets as a dietary supplement.

In another embodiment of the invention, the composition is administered to a human in a pharmaceutical composition.

In another aspect, the invention is a method of altering the concentration of cholesterol constituents in the blood of a human, to preferably reduce the risk of atherosclerosis and vascular disease, where the composition is administered to a human in an amount effective to increase the concentration of HDL-cholesterol in the blood of the human. Reducing cholesterol levels with the administration of this composition can also prevent other plaque formation and other types of atherosclerotic disease such as the cereberovascular complications of carotid artery plaques, peripheral vascular disease and claudication, and intestinal vascular blockage and infarction.

DETAILED DESCRIPTION OF THE INVENTION

Hyperlipidemia relates to plasma cholesterol and triglyceride levels that exceed "normal"—arbitrarily defined as the $95^{th}$ percentile. But it is now clear that "ideal" or "optimal" levels are far below the normal levels of the population. A large proportion of United States adults have concentrations above the optimal range and should be considered to have hyperlipoproteinemia. J. Hardman, supra, at 875.

In a preferred embodiment of the invention, a composition is administered that simultaneously affects several different mechanisms in the production of atherosclerosis, including the levels of LDL and HDL cholesterol, through inhibiting HMG-CoA Reductase, correcting any consequent depletion of Coenzyme $Q_{10}$, and inhibiting the oxidation of LDL into lipid peroxidases. In another embodiment, chromium or inositol hexanicotinate, or both, is added for control of insulin and lipid metabolism and additional control or reduction of cholesterol levels.

One theory is that both the presence of elevated plasma LDL and its oxidative modification within the artery wall is required to produce atherosclerosis. Steinberg, supra. Indeed, then the use of an appropriate antioxidant in vivo should decrease the rate at which LDL is taken up by macrophage foam cells and slow the development of the fatty streak lesion. This phenomena has been demonstrated in receptor deficient rabbits treated with Probucol as an antioxidant. Parthasarathy, supra.

Red yeast is a mixture of several species of *Monascus* fungi; the predominant one is *Monascus purpureus*. *Monascus* was first described in 1884. Van Tieghem, 31 BULL. SOC'Y BOTANY FRANCE 226 (1884). *Monascus* has been used for centuries as in wine fermentation and as a food colorant and preservative. See http://www.allok.com/ehistorie.htm. A traditional Chinese product used to make rice wine and as a preservative is based on rice that has been fermented with *Monascus purpureus*. Heber, 69 AM. J. CLINICAL NUTRITION 231–236 (1999), citing STUART, CHINESE MATERIA MEDICA-VEGETABLE KINGDOM (1979). This product also has a tradition of being useful in "improving the blood circulation." D. Bensly & R. Barolet, CHINESE HERBAL MEDICINE: MATERIA MEDICA (Revised Ed. 1993).

The medical applications of red yeast were described in the ancient Chinese pharmacopoeia, Pen Ts'ao Kang Mu, published during the Ming dynasty (1368–1644). It describes red yeast as useful for treating indigestion, diarrhea, and improving the health of the spleen, stomach, and circulation. In Ancient China, *Monascus* was called "Hongqu" and was said to have the ability to cure stomach and spleen, to strengthen the blood, and the principle to preserve and endorse the common Qi interdependent. BEN CAO GANG MU VON LI SHI-ZEN, BOOK OF MEDICINAL HERBS (1590).

More recently, researchers discovered that a strain of *Monascus* yeast used in the production of red yeast rice naturally produced a substance that inhibits cholesterol synthesis called Monacolin K (lovastatin), along with a group of 8 Monacolin-related substances that are HMG-CoA Reductase inhibitors. Endo, supra. Experiments in rabbits revealed that one extract, Xuezhikang, lowered cholesterol levels by 44% and 59% at doses of 0.4 and 0.8 mg/kg, respectively. Id., see also Li, 18(1) NUTRITION RESEARCH 71–81 (1998). These doses correspond to human doses of 24 mg and 48 mg (for a 60-kg person). Chinese red yeast rice costs only $20–30 per month at such doses, compared to the average cost of $187/month for a cholesterol-lowering drug. Id.

The effects of *Monascus purpureus* rice in 324 patients were compared with the effects of another Chinese herbal medicine, Jiaogulan (gynostemma pentaphylla) on serum cholesterol. Wang, 58(12) CURRENT THERAPEUTIC RESEARCH 964–978 (1997). Eligible patients were recruited if their serum total cholesterol (TC) was 240 mg/DL (5.95 mmol/L) or higher, LDL-cholesterol was 130 mg/dL (3.41 mmol/L), or triglycerides (TG) were 200–400 mg/dL (2.26–4.52 mmol/L). In addition, HDL-cholesterol was 40 mg/dL (1.04 mmol/L) or less for men or 45 mg/dL (1.16 mmol/L) for women. After 8 weeks, total cholesterol decreased by 34.5% ($P<0.001$) in treated patients while the positive controls had only an 8.3% decrease. Those patients with pretreatment cholesterol over 300 mg/dL had a greater reduction than did those whose cholesterol prior to treatment was below 240 mg/dL. And while the increase in HDL cholesterol was minor for those with pre-treatment levels>45 mg/dL, significant increases were observed in those with pretreatment HDL of 35–45 mg/dL (16%) and less than 35 mg/dL (25.1%).

Coenzyme $Q_{10}$ (Ubiquinone) is a naturally occurring substance that plays a central role in oxidative respiration as a catalyst and has a separate direct membrane stabilizing effect. In man, vitamin E, beta-carotene, and Coenzyme $Q_{10}$ all appear to be endogenous antioxidants in LDL. Epidemiologic data suggest a negative correlation between coronary disease and levels of vitamin E. Witztum & Steinberg, supra. It is also an antioxidant and free radical scavenger, and protects ischemic tissue from the damage that occurs when blood flow is restored (reperfusion damage). In studies of cardiac patients, deficiencies of the enzyme were found in 75% of 132 biopsy specimens of heart tissues, and 20% of 406 blood samples. Studies performed by several different groups of researchers have shown that supplementation with Coenzyme $Q_{10}$ improves the signs and symptoms of CAD at doses of 1.5 mg/kg per day (90 mg in a 60 kg person), 150 mg/day and 600 mg/day. Greenberg & Frishman, 30 J.

CLINICAL PHARMACOLOGY 596–608 (1990) at p. 599. Earlier clinical studies in Japan used a dose of 5 mg, and later a dose range of 25–100 mg. Folkers, et al., 2 J. MOLECULAR MEDICINE 431–460 (1977).

Coenzyme $Q_{10}$ and alpha-tocopherol in the LDL cholesterol are depleted faster on lovastatin therapy during peroxidative insult. The finding was associated with a shortened lag time of conjugated diene formation suggesting diminished resistance of LDL particles to the early phase of oxidative stress. A crossover study was conducted to investigate the effects of supplementation with 180 mg per day Ubiquinone (Coenzyme $Q_{10}$). There were no differences in the measurements for cholesterol, LDL, HDL, the LDL/HDL ratio, triglycerides, or apolipoprotein levels between treatment arms. But in the oxidative studies, the total depletion time of LDL Coenzyme $Q_{10}$ was 49.6% longer on lovastatin but was comparable to pre-treatment levels with supplementation. The authors concluded that the improvement was scarce and its clinical relevance remained open. Palomaki, 39 J. LIPID RESEARCH 1430–1437 (1998). In men with familial combined hyperlipidemia, LDL was more prone to oxidation and the Coenzyme $Q_{10}$ in the LDL was more predominantly in a reduced state, suggesting the Coenzyme $Q_{10}$ plays an important role in protecting LDL from in vivo oxidation. de Rijke, 17(11) ARTERIOSCLEROSIS, THROMBOSIS, AND VASCULAR BIOLOGY 127–133 (1997). This was studied by comparing patients treated with 20-mg simvastatin per day with or without supplementation with Coenzyme $Q_{10}$ at 100 mg per day. In both groups, both total cholesterol and LDL cholesterol declined and results were highly statistically significant. But levels of Coenzyme $Q_{10}$, which started out similar, decreased in the group treated with simvastatin alone, yet increased in the group that was supplemented. Bargossi, 15 MOLECULAR ASPECTS OF MEDICINE s187–s193 (Supp. 1994).

Minimally oxidized LDL is believed to be involved in the early stages of atherosclerosis. In several studies of the HGM-CoA Reductase induced Coenzyme $Q_{10}$ eficiency, supplementation with coenzyme $Q_{10}$ at 100 mg to 180 mg was shown to correct the depletion of the enzyme within the LDL particle. Id. Supplementation with Coenzyme $Q_{10}$, 100 mg per day for 30 days resulted in increased Coenzyme $Q_{10}$ levels in all three LDL subfractions (P<0.01) in each of the 10 subjects studied. Small increases in vitamin E were observed, as well as a significant decrease in hydroperoxide levels in the $LDL_3$ subfraction, which is commonly elevated in patients at high risk for coronary artery disease. Alleva, 92 PROC. NAT'L ACAD. SCI. 9388–9391 (1995).

In an open label, eight-year study, 424 patients with various forms of cardiovascular disease added Coenzyme $Q_{10}$, 75 mg to 600 mg/day, to their diets. Improvements in myocardial function (58%) and decreased dependency on drugs (43%) were noted. Langsjoen, 15 MOLECULAR ASPECTS OF MEDICINE s165–s175 (Supp. 1994).

Several prospective studies suggest an inverse association between dietary intake or plasma concentrations of antioxidants and CVD. In a cross-cultural study of 16 European populations, the strongest inverse correlation in this study was observed between ischemic heart disease and plasma concentration of vitamin E, a well-established anti-oxidant. Meydani, 345(8943) LANCET 170–175 (1995). However, two earlier studies in Finland and the Netherlands reviewed by Meydani in 1995 did not find an association between serum vitamin E and subsequent CVD mortality. In men, a borderline significant association was found for dietary intake of vitamin E alone, but it was much stronger for vitamin E supplement users consuming above 100 IU vitamin E daily for at least 2 years. Id.

In their review of published studies, Jha et. al, reported, inter alia, the results of the U.S. Nurses' Health Study. This study followed 87,000 female nurses for an average of 8 years. About 13% of women regularly used vitamin E supplements. These women, after adjustment for age, smoking, alcohol use, menopausal status, hormone use, exercise, aspirin use, hypertension, cholesterol intake, diabetes, caloric intake, and vitamin C and beta-carotene intake, had a statistically significant reduction in relative risk of 31% (95% confidence limit, 3%, to 51%) for non-fatal myocardial infarction and death from cardiovascular disease in comparison with women who did not use the supplements. The absolute risk reduction was 3.4 women per 10,000 woman-years (a woman-year is one woman followed for one year) of follow-up (8.5 compared with 5.2 per 10,000 woman-years of follow-up). Jha, et al., 123(11) ANNALS OF INTERNAL MEDICINE 860–872 (1995).

Vitamin E is a mixture of tocopherols. D-alpha-tocopherol has the highest biological activity and is the most widely available form of vitamin E in food. The other isomers (beta, gamma, and delta) are less biologically active than d-alpha-tocopherol. The commercially available synthetic forms of vitamin E comprise an approximately equal mixture of eight stereoisomeric forms of alpha-tocopherol. For practical purposes, 1 international unit (IU) of vitamin E is referred to as I mg of the synthetic form, racemic alpha-tocopheryl acetate, and the natural form of d-alpha-tocopherol has a biopotency of vitamin E equal to 1.49 IU. Vegetables and seed oils including soybean, safflower and corn, sunflower seeds, nuts, whole grains, and wheat germ are the main sources of the tocopherols. Meydani, supra.

Researches have observed a relation between deficient selenium (an antioxidant) and an excess risk of acute myocardial infarction as well as death from CHD and CVD in Eastern Finland. Low serum selenium levels and lipid peroxidation in vivo are associated with accelerated progression of carotid atherosclerosis in Eastern Finnish men. In a 1994 study, Salonen reported that a subject's hair mercury content correlated most strongly of all cardiovascular risk factors. Mercury forms an insoluble complex with selenium (mercury selenide), thus binding selenium in an inactive form that cannot serve as a cofactor for glutathione peroxidase, an important scavenger of peroxides and lipid peroxides. Salonen, 91(3) CIRCULATION 645–655 (1995). But another study based on 251 subjects who had infarctions and an equal number of healthy controls matched by age, smoking status, and time from randomization, showed no statistical association between plasma selenium and myocardial infarction. Salvini, 76(17) AM. J. CARDIOLOGY 1218–1221 (1995).

Deficiency of chromium, a trace element, has been associated with lipid abnormalities and an increased risk of atherosclerotic disease. Newman measured serum chromium levels in 32 subjects referred for selective coronary arteriography. Patients with catheterization-proven coronary disease had significantly lower serum chromium levels and higher serum triglyceride (TG) than patients without coronary disease. Newman HA, et. al. 24(4) CLINICAL CHEMISTRY 541–4 (1978).

Chromium is a cofactor in the maintenance of normal lipid and carbohydrate metabolism and its supplementation in normal volunteers has been shown to reduce the levels of total cholesterol, LDL, and apolipoprotein B, and raise levels of HDL. Press, Geller & Evans, 152(1) WESTERN J. MEDICINE 41–5 (1990). Chromium and two molecules of nicotinic acid form a biologically active complex referred to as "glucose tolerance factor," which has been reported to enhance the action of insulin. Jeejeebhoy confirmed the its importance in humans when he successfully treated an insulin-resistant diabetic patient with only chromium supplementation after she had become chromium deficient after 3 years of parenteral nutrition. See Lee & Reasner, 17(12) DIABETES CARE 1449–1452 (1994). An increase in HDL cholesterol levels was observed after chromium treatment in 23 healthy volunteers and in 72 hypertensive men on beta-blockers. Id.

Other groups have shown chromium to improve the lipid profile, hyperglycemia, and body weight in persons with obesity or diabetes. Type 2 diabetics were treated with 100-mcg chromium BID or 500 mcg BID or placebo. The higher dose group showed lower blood sugar and cholesterol than the placebo group after 2 and 4 months. Anderson, 46(11) DIABETES 1786–91 (1997). Chromium supplementation is also useful for elevated triglycerides. In a prospective, double-blind, cross-over study of 14 men and 16 women supplementation with chromium picolinate for 2 months resulted in a statistically significant reduction in triglyceride levels of 17.4% (133 vs. 161 mg/dl; P<0.05). Lee & Reasner, supra.

Inositol hexaphosphate is a form of nicotinic acid that does not produce a flush. Nicotinic acid (niacin, a water-soluble B vitamin) has been shown to decrease triglyceride, increase HDL cholesterol, lower LDL cholesterol, and decrease lipoprotein(a); it also decreases fibrinogen. Gotto Jr., 82(9A) AM. J. CARDIOLOGY 22Q–25Q (1998). It was also shown to increase levels of HDL-cholesterol by 35%, to 1.20+/−0.21 mmol/liter (46.5+/−8.1 mg/dl) at a mean dose of 2,250 mg/day. Zema, 35 (3) JOURNAL OF THE AMERICAN COLLEGE OF CARDIOLOGY 640–6 (2000).

Nicotinic acid was first reported to be hypolipidemic in 1955. Large doses (3 to 6 g/day) rapidly decrease VLDL and LDL and dramatically increase HDL even as much as 20 or 30 mg/dL. But it causes numerous side effects, most importantly an intense flushing and pruritis. Abnormalities of hepatic function, including jaundice, are potentially serious and can occur with 2-g day or delayed-release products. Elevated fasting glucose and delayed glucose tolerance occur frequently and rare side effects include reversible optic maculopathy, toxic amblyopia, arrhythmias, and orthostatic hypotension. See J. Hardman at pp.889–90.

Probucol, a potent antioxidant, was marketed for several years as a hypolipidemic but is now considered only a second or third line agent because of its erratic LDL response and persistent ability to lower HDL levels. It inhibits atherosclerosis in hypercholesterolemic rabbits and non-human primates independently of its hypolipidemic effects, supporting the hypothesis that oxidation is a key step in its development. J. Hardman, supra, at pp. 891–2. Short-term adverse effects include gastrointestinal symptoms, headache, dizziness and increase in the QT interval I many patients.

All of the ingredients used in the compositions of the present invention are obtainable commercially by suppliers well known to those skilled in the art of nutritional supplement formulation. Red yeast rice, although also commercially available, may alternatively be prepared by traditional means.

Indeed, the solid state fermentation of rice by *Monascus* has a long tradition in East Asian countries; its fermentation dates back at least to the first century AD. Heber, supra. The fermentate is obtained as scarlet to purple red grains, which have the original rice grain structure well preserved. The commercial product is mostly a ground powder, which is know as "Ang Kak" or "Hong Qu" in Chinese The Japanese name for the product is "Koji".

Traditional or improved red yeast can be prepared by traditional fermentation procedures or their modification. In Ancient China, *Monascus* was called "Hongqu" and was first described in the 16$^{th}$ century. B.C.G.M. VON LI SHIZHEN, BOOK OF MEDICINAL HERBS (1590). It was said to have the ability to cure stomach and spleen, to strengthen the blood, and the principle to preserve and endorse the common Qi interdependent. Id. The preparation of Hongqu was described as follows:

You take 1 Dan and 5 Dou Jing Mi [the rice]. Clean this with water in a bowl and let it soak for one night. Then you'll cook it like normal food. Further you separate [the rice] in 15 portions and add Jin Pilzmutter. Roll and knead [the mass] to distribute all equally. Form [all] together to one portion and cover it carefully with a silkcloth. First heat [the whole], then take off the silk and splay [the rice pulp]. If the rice pulp is warm, push it together to a heap. Again cover it carefully [with a silkcloth]. Next day at noon again make three heaps [of the pulp], let it rest for a while and form of each part five heaps. Let it rest a short time. Then form all together to a heap. Then let it rest for w while. Then form 15 pieces. Heat a little and then form again a heap. Repeat this 5 times. At the third day fill a big tun with fresh water. Dip short time and process wet and form again a heap. Handle again with this method. At the fourth day again dip it in fresh water If the fungus falls for half and swim for half at the surface, then again use the method from above: Dip shortly. If the fungus completely is at the surface, it's ready. Take it out and dry it in the sun. If this rice responds, we call it shenghuang, a fresh Yellow Color. If you add Hongqu to alcohol, fish sauces or hacked meat, it results a fresh and appealing red. If it doesn't appeal to the heart his quality isn't very well. If added to medicaments, take stored, old Hongqu, that's good.

http://www.allok.com/ehistorie.htm, quoting von li Schizhen, supra.

According to another early reported method (SUNG, T'IEN KUNG K'AI WU 291–294 (1637, Sun trans. 1966)), red yeast can be prepared by the fermentation of washed and cooked non-glutinous rice using red wine mash, natural juice of Polygonum grass, and alum water. The rice is fermented in open air for 7 days on bamboo trays under very clean conditions. The rice changes its color from white to black, black to brown, and brown to red and then red to yellow, which is then harvested as red yeast. According to an alternative traditional method, non-glutinous rice can be fermented in a hole in the ground lined by bamboo mats, which is securely covered. Fermentation is allowed to take place underground for one year or more, up to four years. WO 98/14177 (1998), at p. 9.

The traditional method has been improved with modern fermentation techniques and equipment to more precisely control temperature, pH, pressure and other fermentation parameters thus reducing the time required. One example is as follows: culture media containing kidney-bean juice 2%, sugar 4%, yeast 0.5% are added to rice (40–80 ml per 100 g) and sterilized by heat while the pH is maintained at pH3 to 8. Red yeast fungi *Monascus purpureus* Went strain M4184 is added and cultured at 15–35° C. for 9 days. At the end of the fermentation process, the fermentation broth is drained and discarded, while the solid residue is sterilized by heat, dried and crushed into powder. Id. This powder can be used directly in the various compositions and formulations provided in the present invention.

*Monascus purpureus* is available commercially around the world, through distributors such as Dr. Winfried Behr at Friedrich-Breuer-Str. 86-D-53225 Bonn, Allok at Lachenmeyrs TR. 18a, 81827, Munchen, Germany and Samlong Chemical Co., Ltd., P.B. Box 65, Changzhou, Jiangsu, China.

Coenzyme $Q_{10}$, mixed tocopherols (vitamin E), selenium, chromium, and inositol hexaphosphate are available commercially, in bulk and wholesale, from suppliers well known to those with ordinary skill in the art. For instance, Vitamin E may be obtained from Ava Health PO Box 730, Grove City, Ohio 43123-0730 and Wholesale Vitamins USA, Inc., of Brooklyn, N.Y. offers over 8,000 vitamins at wholesale prices.

Any dosage form may be employed for providing the patient with an effective dosage of the composition. Dosage forms include tablets, capsules, dispersions, suspensions, solutions, capsules, transdermal delivery systems, etc. . . Tablets and capsules represent the most advantageous oral dosage unit form. Any method known to those of ordinary skill in the art may be used to prepare capsules, tablets, or other dosage formulations. Pharmaceutically acceptable carriers include binding agents such as pregelatinized maize starch, polyvinylpryrrolidone or hydroxypropyl methycellulose; binders or fillers such as lactose, pentosan, microcrystalline cellulose or calcium hydrogen phosphate; lubricants such as magnesium stearate, talc or silica; disintegrants such as potato starch or sodium starch; or wetting agents such as sodium lauryl sulfate. Tablets or capsules can be coated by methods well known to those of ordinary skill in the art.

According to one aspect of the invention a composition is provided comprising a pharmaceutically acceptable combination of the composition and at least one carrier. Pharmaceutically acceptable carriers for inclusion into the present compositions include carriers most suitable for combination with lipid-based drugs such as diluents, excipients and the like which enhance its oral administration. Suitable carriers include, but are not limited to, sugars, starches, cellulose and derivatives thereof, wetting agents, lubricants such as sodium lauryl sulfate, stabilizers, tabletting agents, antioxidants, preservatives, coloring agents and flavoring agents. Reference may be made to REMINGTON'S PHARMACEUTICAL SCIENCES, (17th ed. 1985) for other carriers that would be suitable for combination with the present compositions. As will be appreciated, the pharmaceutical carriers used to prepare compositions in accordance with the present invention will depend on the administrable form to be used.

According to one embodiment of the invention, the novel composition of the present invention comprises red yeast fermented on rice, Coenzyme $Q_{10}$, chromium, selenium and mixed tocopherols and inositol hexanicotinate, and is formulated for oral administration. Oral dosage forms formulated in accordance with standard pharmaceutical practice may be employed. Capsules are a particularly useful vehicle for administering the present composition. The administration of the composition is preferably in accordance with a predetermined regimen, which may be at least once daily and over an extended period of time as a chronic treatment, and could last for one year or more, including the life of the host. The dosage administered will depend upon administration frequency, the blood level desired, In a preferred aspect of the invention, a composition of the present invention is administered to reduce or control blood cholesterol levels in persons having a total cholesterol of 240 mg/DL (5.95 mmol/L) or higher. In another embodiment of the invention, the compositions are administered to reduce levels of LDL-cholesterol in persons with an LDL-cholesterol of 130 mg/dL (3.41 mmol/L) or higher. In yet another embodiment of the invention, the compositions are administered to reduce triglycerides in persons having blood triglycerides of 200 mg/dL (2.26 mmol/L) or higher. In another embodiment, a composition of the present invention is administered to raise levels of HDL to persons with an HDL-cholesterol of 35 mg/dL (1.04 mmol/L) or lower to reduce the risk of atherosclerosis associated with low HDL levels. The compositions and methods of the present invention may also be utilized to improve or maintain vascular health in specific organ systems including the cardiovascular system, the cereberovascular system, the peripheral vascular system and the intestinal vascular system.

According to an additional embodiment, the compositions of the present invention may be admixed by conventional methods and may be administered by an alternative route such as suppository, spray, liquid, powder, liposome, dermal patch, and inhalant. These methods are well known to those skilled in the art. For example, liposomes may be formulated according to methods such as those of U.S. Pat. No. 5,853,755, to Foldvari, U.S. Pat. No. 4,235,871 to Papahadjopoulos, et al, or U.S. Pat. No. 4,708,861 to Popescu et al (liposome-gel combination). Sublingual and transdermal methods are also well known to those skilled in the art, e.g., U.S. Pat. No. 5,922,342 to Shah, et al describes a sublingual formulation and U.S. Pat. No. 4,997,655 to Nagy, et al describes a transdermal administration method.

In a specific embodiment of the invention, the composition comprises between 50 mg and 3.6 gm red yeast rice, between 5 and 300 mg coenzyme Q10, between 10 mcg and 1 mg chromium, between 5 and 1 g inositol, between 10 mcg and 1 mg selenium, and between 5 IU and 800 IU mixed tocopherols. In yet another embodiment of the invention, the composition comprises between 100 mg and 2.4 gm red yeast rice, between 5 and 250 mg coenzyme Q10, between 10 mcg and 500 mcg chromium, between 10 and 800 mg inositol, between 10 mcg and 500 mcg selenium, and between 5 IU and 400 IU mixed tocopherols. In yet another embodiment of the invention, the composition comprises between 100 mg and 1.2 gm red yeast rice, between 5 and 150 mg coenzyme $Q_{10}$, between 10 mcg and 300 mcg chromium, between 20 and 500 mg inositol, between 10 mcg selenium, and between 5 IU and 200 IU mixed tocopherols. And in yet another embodiment of the invention, the composition may be administered in a daily dose of between 50 mg and 1.6 gm red yeast rice, between 10 and 600 mg coenzyme Q10 and between 5 IU and 800 IU mixed tocopherols.

In a preferred embodiment, the composition is administered in four tablets each comprising about 500 mg red yeast rice, about 15 mg coenzyme $Q_{10}$, about 50 mcg chromium, about 13 mg inositol, about 50 mcg selenium, and about 20 IU mixed tocopherols to provide a total daily dose of about 2 gm red yeast rice, about 60 mg Coenzyme $Q_{10}$, about 200 mcg chromium, about 52 mg inositol, about 200 mcg selenium and about 80 IU mixed tocopherols.

The administration of the composition would be in accordance with a predetermined regimen, which would be at least once daily and over an extended period of time as a chronic treatment, and could last for one year or more, including the life of the host. The dosage administered will depend upon the frequency of the administration, the blood level desired, other concurrent therapeutic treatments, the severity of the condition, whether the treatment is for prophylaxis or therapy, the age of the patient, the levels of LDL-cholesterol and HDL-cholesterol in the patient, and the like.

The invention will be further illustrated by the following non-limiting examples:

EXAMPLE 1

A study of the effect of the red yeast rice, 200 mg QID, Coenzyme $Q_{10}$ 10 mg QID, mixed tocopherols 10 IU QID, selenium 20 mcg QID, chromium 20 mcg QID, and inositol 20 mg QID on HDL-cholesterol, non HDL-cholesterol, and total cholesterol concentrations in the blood of men with elevated cholesterol levels is conducted over a 6 month period. A statistical analysis is performed to compare the resulting cholesterol levels of the test and a control (placebo) group to determine if a significant improvement in cholesterol levels results from administration of the test preparation.

Sixty men having total plasma cholesterol of between 240 and 300 mg/dL are selected for inclusion in the statistical study. Two weeks prior to the start of the study each subject completes a two day dietary intake record and is interviewed by a Registered Dietitian to calculate each individual's daily energy requirement for a basal low fat, low cholesterol National Cholesterol Education Program Step I diet. Each subject is given a booklet published by the American Heart Association containing a long list of foods, along with a calculated "fat gram prescription" which complies with the criteria for the basal diet.

All subjects follow the basal diet for a period of at least fourteen days. After this, baseline blood samples are drawn on two separate days, and the subjects are randomly assigned to one of two treatment groups, the test capsules or matching placebo capsules. Both groups continue on their basal diet and incorporate four tablets of the test composition in the diet.

The effects of the dietary supplementation on total cholesterol, HDL-cholesterol, and non-HDL cholesterol, as well as dietary intake, body mass index, and physical activity are evaluated using multiple linear regression analysis and a standard students t-test. In each analysis the baseline value of the outcome variable is included in the model as a covariant. Treatment by covariant interaction effects is tested by the method outlined by Weigel & Narvaez, 12 CONTROLLED CLINICAL TRIALS 378–94 (1991). If there are no significant interaction effects, the interaction terms are removed from the model. The regression model assumptions of normality and homogeneity of variance of residuals are evaluated by inspection of the plots of residuals versus predicted values. Detection of the temporal outset of effects is done sequentially by testing for the presence of significant treatment effects at 18, 12, and 6 weeks, proceeding to the earlier time in sequence only when significant effects have been identified at each later time period. In addition, differences between groups in nutrient intake, physical activity, and body mass index (ht/wt.sup.2) at each time point are compared using one-way analysis of variance. Changes from the baseline within each group are evaluated using paired t-tests. In addition, analysis of variance is performed on all baseline measurements and measurable subject characteristics to assess homogeneity between groups. All statistical procedures are conducted using the Statistical Analysis System (SAS Institute Inc., Cary, N.C.). An alpha level of 0.05 is used in all statistical tests.

A statistically significant increase in HDL-cholesterol and the decrease in non-HDL cholesterol including LDL-cholesterol are observed in the blood of the treated subjects upon completion of the study but not the controls. The differences between the levels of HDL-cholesterol and non-HDL cholesterol including LDL-cholesterol in the treated subjects and controls are statistically significant.

EXAMPLE 2

A composition of the following formulation was prepared in table form by standard methods:

| Red yeast rice | 500 mg |
| Coenzyme $Q_{10}$ | 15 mg |
| Mixed tocopherols | 20 IU |
| Selenium | 50 mcg |
| Chromium | 50 mcg |
| Inositol | 13 mg |

4 tablets per day is the recommended dosage for an average weight adult human (70 - kg).

The invention has been described in detail with particular reference to preferred embodiment thereof. However, it will be appreciated that those skilled in the art, upon consideration of this disclosure may make variations and modifications within the spirit and scope of the invention.

I claim:

1. A composition comprising between 50 mg and 3.6 gm red yeast rice, between 5 mg and 600 mg coenzyme Q10, and between 5 IU and 400 IU mixed tocopherols.

2. The composition of claim 1 wherein said composition is in a dosage form selected from the group consisting of a tablet, capsule, liquid, liposome, inhalant, sublingual tablet, suppository, oral spray and dermal patch.

3. The composition of claim 1 further comprising a pharmaceutically acceptable carrier.

4. The composition of claim 1 wherein said red yeast fermentation on rice is produced from the fermentation of one or more of the group of red yeast consisting of *Monascus purpureus, Monascus ruber, Monascus fuliginosus, Monascus Pilosus,* and *Monascus albidus*.

5. The composition of claim 1 comprising between 100 mg and 2.4 gm red yeast rice, between 5 mg and 250 mg coenzyme $Q_{10}$, and between 5 IU and 400 IU mixed tocopherols.

6. The composition of claim 5 comprising between 100 mg and 1.2 gm red yeast rice, between 5 mg and 150 mg coenzyme $Q_{10}$, and between 5 IU and 200 IU mixed tocopherols.

7. The composition of claim 1 further comprising one or more selected from the group consisting of selenium, chromium, and inositol hexanicotinate.

8. The composition of claim 7 wherein the chromium is chromium picolinate.

9. The composition of claim 7 wherein the chromium is chromium tripicolinate.

10. The composition of claims 7 comprising between 50 mg and 3.6 gm red yeast rice, between 5 mg and 600 mg coenzyme $Q_{10}$, between 10 mcg and 1 mg chromium, between 5 mg and 1 gm inositol, between 10 mcg and 1 mg selenium, and between 5 IU and 800 IU mixed tocopherols.

11. The composition of claim 10 comprising between 100 mg and 2.4 gm red yeast rice, between 5 mg and 250 mg coenzyme $Q_{10}$, between 10 mcg and 500 mcg chromium, between 10 mg and 800 mg inositol, between 10 mcg and 500 mcg selenium, and between 5 IU and 400 IU mixed tocopherols.

12. The composition of claim 11 comprising between 100 mg and 1.2 gm red yeast rice, between 5 mg and 150 mg coenzyme $Q_{10}$, between 10 mcg and 300 mcg chromium, between 10 mg and 500 mg inositol, between 10 mcg and 300 mcg selenium, and between 5 IU and 200 IU mixed tocopherols.

13. The composition of claim 12 comprising about 500 mg red yeast rice, about 15 mg coenzyme $Q_{10}$, about 50 mcg chromium, about 13 mg inositol, about 50 mcg selenium, and about 20 IU mixed tocopherols.

* * * * *